United States Patent [19]  [11] 3,954,964
Kuderna, Jr.  [45] May 4, 1976

[54] AIR REODORANT COMPOSITIONS

[75] Inventor: Jerome G. Kuderna, Jr., Modesto, Calif.

[73] Assignee: Shell Oil Company, Houston, Tex.

[22] Filed: Mar. 4, 1974

[21] Appl. No.: 448,127

[52] U.S. Cl. .................................. 424/76; 239/60; 252/522
[51] Int. Cl.² ...................... A61L 9/00; A61L 9/04; A61L 13/00
[58] Field of Search ...................... 424/76; 252/522

[56] References Cited
UNITED STATES PATENTS

| | | | |
|---|---|---|---|
| 2,691,615 | 10/1954 | Turner et al. | 424/76 |
| 2,865,806 | 12/1958 | Bulloff | 424/76 |
| 2,927,055 | 3/1960 | Lanzet | 424/76 |
| 3,655,129 | 4/1972 | Seiner | 424/76 X |
| 3,688,985 | 9/1972 | Engel | 239/54 |
| 3,821,413 | 6/1974 | Hellyer, Jr. | 424/76 X |

FOREIGN PATENTS OR APPLICATIONS 1,241,914  8/1971  United Kingdom

OTHER PUBLICATIONS

The Merck Index, 8th Ed., (1968), pp. 214, 215, 654.

*Primary Examiner*—Jerome D. Goldberg
*Assistant Examiner*—Allen J. Robinson

[57] ABSTRACT

Long lived, slow-release air reodorant compositions comprise polyvinyl acetal resins gelled with alkyl salicylates. The gels may additionally contain one or more fragrances or perfumes, diluents or adjuvants, a minor amount of water, as well as dyes, surfactants, deodorants and other conventional additives.

9 Claims, No Drawings

AIR REODORANT COMPOSITIONS

RELATED APPLICATIONS

This application is related to copending Ser. No. 448,126 filed of even date herewith which claims similar organically gelled air reodorants differing primarily in the gelling agent used.

BACKGROUND OF THE INVENTION

Air reodorizing or deodorizing compositions in gel form are well-known in the art. Primarily they comprise an aqueous medium containing a volatile fragrance and a small amount of a gelling agent which renders the compositions in a gel-like or semi-solid form. These compositions are popular in that they are easy to handle, and on exposure to air, the aqueous medium gradually evaporates from the gel releasing the fragrance into the surrounding atmosphere. Aqueous gels of this type are claimed in U.S. Pat. Nos. 2,691,615 and 2,927,055 and in British Pat. No. 1,241,914.

One difficulty with most aqueous gels is that they are relatively short-lived. This is because of the rapid rate of release of water and fragrance from gels of this type, and because only a small part of the gel, i.e., from 1 to 10% of the aqueous phase, is available as a fragrance for acting as a reodorant. Also, because of the rapid rate of release of water, aqueous gels are necessarily large in size, thus limiting holder design and increasing shipping costs. Moreover, when subjected to low temperatures the aqueous gels might freeze which will result in excessive bleeding or gel decomposition upon thawing. In addition, aqueous gels are subject to microbial degradation.

As used in this application, the term "reodorant" means an air freshener whereby the odors in the surrounding atmosphere are masked or overcome by the fragrance emitted from the air freshener. As so defined this term is intended to include true deodorants which react with or destroy the odor which is to be overcome.

Various types of non-aqueous air fresheners have also been proposed. For example, U.S. Pat. No. 2,865,806 discloses an air odor control agent prepared by blending a menthadiene compound, and preferably an added antioxidant, with a selected solidifying agent at an elevated temperature and then cooling the blend. The solidifying agents are certain polyethylenes and ethyl celluloses. The menthadiene compounds are monocyclic terpenes containing nonconjugated double bonds, not more than one of which occurs outside the six carbon ring, i.e., d- or l-limonene or racemic mixtures (dipentene) may be used. An important feature of the disclosed non-aqueous air fresheners is said to be that bleeding or exudation of the dipentene to the surface of the molded product occurs which facilitates its removal from the mold.

While bleeding or exudation may be beneficial in aiding the release of the molded product, these properties are generally not desirable to the consumer since syneresis or bleeding during use can cause liquid droplets to come in contact with fabrics, furniture and other finishes within the home which may cause staining or other damage. Hence, from a consumer point of view, it is desirous to have a solid air reodorant which is storage stable, dry to the touch and yet which permits adequate release of a fragrance into the surrounding atmosphere over a sustained period of time.

An attempt to achieve these results is outlined in U.S. Pat. No. 3,688,985 wherein a pre-formed-plastic object is soaked in a stable aqueous emulsion containing an essential oil and a surfactant to impregnate the resin with the essential oil thereafter drying the resin to yield a dry impregnated resin which gradually releases the essential oil into the surrounding atmosphere.

Also mentioned in U.S. Pat. No. 3,688,985 is British Pat. No. 599,237 wherein an essential oil is combined with a plasticized synthetic resin by dispersing the resin in a plasticizer, including the essential oil, which is gelled by heat to form the desired article. However, as reported, the essential oils when heated to the gelling temperatures break down, thereby causing a change in the chemical properties of the essential oil so that it can no longer be useful for the intended purpose.

Thus it can be seen that although considerable effort has been devoted to the development of stable, long-lived air reodorant formulations, considerable problems remain and there is continuing need for improved products. The present invention is directed to one such class of highly advantageous air reodorant compositions.

STATEMENT OF THE INVENTION

It has now been found that storage stable, dry, long lived air reodorant compositions can be made comprising certain resin bases which have been gelled with a particular class of organic gelling agents. More specifically, it has been found that when polyvinyl acetal resins are combined with alkyl salicylates unique gels result having highly beneficial properties as air reodorants. Such gels may additionally contain one or more fragrances or perfumes, diluents or adjuvants, a minor amount of water, as well as dyes, surfactants, deodorants and other conventional additives. The gels generally can be prepared at room temperature but may be heated to an elevated temperature below that at which the gellant, diluent or fragrance decomposes. The resulting organic gels are dry and rubbery in appearance, are storage stable, and release an effective amount of fragrance over extended periods of time in addition to being very compact.

DETAILED DESCRIPTION OF THE INVENTION

Fundamental to this invention is the discovery that alkyl salicylates act as gelling agents for polyvinyl acetal resins having the following properties:

1. The resin must be compatible with the alkyl salicylate gelling agent.
2. The resin should have a molecular weight of from about 30,000 to about 1,000,000 and preferably from about 180,000 to about 300,000.
3. The resin must contain free hydroxyl groups.

While it is not precisely known by what mechanism the alkyl salicylates interacts with the polyvinyl acetal resin, it is believed that the mechanism is that of hydrogen bonding between the ester function of the salicylate and the free hydroxyl functions of the resin. Gel structures so formed have the capability of absorbing relatively large amounts of other liquids including water if adequately solubilized. Therefore although the gelling agents themselves, i.e., the alkyl salicylates, can serve as fragrances, other fragrances may also be added to the gels of the invention thereby providing the opportunity to vary the quality, quantity and intensity of the odor. In other words, practically any odor desired may be produced in the gels of this invention by appropriate selection of fragrance and diluent.

Among the polyacetal resins that can be used according to the invention are polyvinyl formal, polyvinyl acetal and polyvinyl butyral resins. In general, useful polyvinyl acetal resins are these consisting essentially of repeating vinyl acetal, vinyl alcohol and vinyl acetate groups represented by the following chemical structure:

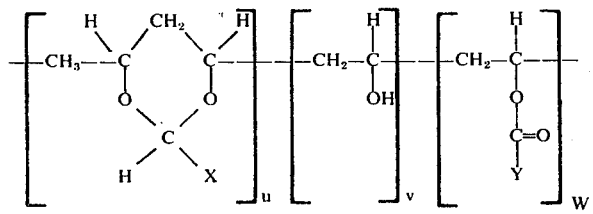

wherein X is H, alkyl, haloalkyl or hydroxyalkyl of 1–8 carbon atoms, alkenyl of 2–8 carbon atoms, halogen or hydroxyl; Y is alkyl of 1–9 carbon atoms; and u, v and w indicate the relative percent by weight of the vinyl acetal, vinyl alcohol and vinyl ester groups, respectively, in the resin.

In order to maintain hydrogen-bonding between the polyvinyl acetal resin and alkyl salicylates as previously discussed, it is necessary that the resin contain a certain number of free hydroxyl groups which will vary somewhat from polymer to polymer. In general, the relative percentage of vinyl alcohol groups (v in the above formula) should be at least 10, preferably from about 15 to about 25, most preferably from about 17 to about 21. The percentage of vinyl acetal groups (u in the above formula) can be from about 30 to about 90, but preferably is from about 75 to about 85, while the percentage of vinyl ester groups (w in the above formula) can vary from 0 to about 30, but preferably is from 0 to about 5. The sum of $u$, $v$ and $w$ equals 100.

Polyvinyl acetal resins having molecular weights and vinyl acetal, vinyl alcohol, and vinyl ester contents within the above specified ranges can be prepared by well known methods and are commercially available. Among the polyvinyl resins which can be employed in the reodorant gel compositions of the invention, polyvinyl butyrals have been found to be particularly advantageous.

Depending upon the odor desired, any alkyl salicylate compatible with the polyvinyl acetal resin can be utilized. Lower alkyl salicylates are preferred, e.g., $C_1$ to $C_8$ alkyl salicylates, particularly methyl salicylate, ethyl salicylate and amyl salicylate.

The alkyl salicylates may be brought into contact with the polyvinyl acetal resins as a separate ingredient or they can be present as a component of the perfume or fragrance which is added to the polyvinyl acetal resin. In other words the means by which the alkyl salicylate gellant and polyvinyl acetal are brought into contact is immaterial so long as the requisite amounts of each are present. Hence, as will be apparent to those skilled in the art, perfumes which contain salicylates as part of their formulation can be suitably employed to form gel compositions in accordance with the present invention, without the need for separate alkyl salicylate addition.

Various diluents may be added to the compositions of this invention and act in many ways to enhance its acceptability. For example, diluents are usually cheaper than the gelling agent and/or fragrances used and at the same time serve to extend the useful life of the gel compositions. In general, any organic diluent having a boiling point of between about 175 and 250°C and which is mutually compatible with the gellant and fragrance can be used in the present invention. As previously mentioned, these diluents should have a pleasant aroma and blend well with the fragrance and gelling agent. Typical of the diluents that may be added in the invention are the menthadienes such as d- and l-limonene. Other diluents include beta pinene, amyl acetate, isopropyl acetate, alpha terpineol, 2-ethylhexyl alcohol and octyl acetate. Some diluents, for example d-limonene, have a citrus odor. Other diluents used in combination with limonene, for example, 2-ethylhexyl alcohol, tend to mask the citrus odor of limonene and therefore make the added fragrance more distinct. In addition, minor amounts of water, e.g., up to about 20% by weight of the total composition, can be employed as diluent if adequately solubilized, e.g., by the addition of one or more surfactants. In general, the organic diluents act the same as water in an aqueous gel formulation except that the organic diluent in itself is a fragrance as well as a carrier. Moreover, the diluent tends to come out of the organically gelled formulation at a slower rate than does water from an aqueous air reodorizer, thereby considerably extending the life of the organically gelled air reodorizer.

The fragrances or perfumes which may be added to the compositions of this invention are many and varied and it would serve little purpose to try to elucidate each and every fragrance which can be utilized herein. The only essential requirements for the fragrances herein employed are that they be mutually compatible with the gellant and resin (and diluent if employed), and that they have mutually compatible odors. In general, the fragrances will have a boiling point between about 150°–350°C, preferably 200°–300°C and will add body and contribute a sophisticated quality to the odor of the gel composition.

Suitable fragrances may be comprised of single chemical constituents or may be blends of many different chemical compounds which may be of natural or synthetic origin. These fragrances include alcohols, aldehydes, ethers, ketones, esters and frequently also hydrocarbons which are combined in fixed proportions so that the odor of the individual compound will combine to produce a harmonious fragrance. In perfumery practice these compounds are combined by the blending of natural essential oils, gums, resins, animal derivatives, natural isolates and synthetic chemicals. In practice, most perfumes are blends of many types of chemicals and their composition is of a proprietary nature and hence normally designated by trade name rather than by chemical composition. Because of this, and since the efficacy of the present gels is not dependent on the use of any particular perfume, no attempt has been made to define the fragrance with the same chemical preciseness as the gellant and resin, nor would it be possible to do so.

From the foregoing it can be seen that the only essential components of the present reodorant compositions are the alkyl salicylate gellant and the polyvinyl acetal resin, since the alkyl salicylate can serve as the fragrance and/or diluent as well as the gellant. However, as previously discussed, it is generally desirable from an economic standpoint to employ an additional diluent, and from a fragrance quality standpoint to employ an additional fragrance (perfume) to supplement and reinforce the odor of the alkyl salicylate gellant and/or diluent.

As also mentioned, alkyl salicylates can be present as a component of a particular perfume or fragrance formulation in which event suitable reodorant gels can be formed from the alkyl salicylate-containing perfume and polyvinyl acetal resin alone, without the need for further salicylate addition.

As will also be obvious from the above description, the major proportion of the liquid in the gels of the present invention is available as a reodorant which has a distinct advantage over aqueous gels wherein only a minor portion of the liquid phase is available for air freshening purposes, the water serving only as a carrier.

In general, the reodorant gel compositions of this invention comprise from about 10 to about 40% by weight of polyvinyl acetal resin and from about 5 to about 90% by weight of the alkyl salicylate gellant. The reodorant gels may additionally contain from 0 to about 60% by weight of organic diluent and from 0 to about 85% by weight of a perfume. Obviously the above proportions are heavily weighted at the upper limits of diluent, perfume and gellant in that, as previously discussed, it is possible for the alkyl salicylates to function as both perfume and diluent as well as gellant. Likewise it is also possible for the fragrance or perfume to also serve as diluent or even gellant, provided it contains the requisite amount of alkyl salicylate.

Within preferred limits the resin will normally comprise about 15 to about 30% by weight of the composition with the gellant comprising about 10 to about 30% by weight of the composition. The diluent, in preferred ranges, will be present in amounts varying from about 10 to about 50% by weight, whereas the fragrance or perfume will be present in an amount of about 1 to about 60% by weight, while water will be present in an amount of from 0 to about 10% by weight.

The amount of resin in the composition is critical to its function. Too little resin will cause the composition not to gel completely or to exhibit certain amounts of syneresis, whereas too much resin will result in a dry blend, i.e., a blend wherein not all of the resin is interacted with the gellant. In other words, the gellant will not completely wet the resin that is available. The final choice of gellant and resin will depend upon the properties desired, the fragrances used and the rate of release that is to be obtained.

While the rate of release of the reodorant from the compositions of this invention may be controlled by the optimization of ingredients contained therein, the rate may be further controlled by physical means. Since the gels function by the migration of the odor-releasing chemicals from within the matrix to the surface of the gel and thence into the surrounding atmosphere, it is obvious that by controlling the available surface area (e.g., through size or geometry) the rate of release of odorants into the atmosphere can be regulated. Therefore, gels having a single surface (such as when contained in a dish or cup having sidewalls) will release its constituents at a slower rate and will be depleted less quickly than will gels having multiple surfaces (such as provided by a cube). Moreover the gels can be wrapped or placed within a barrier such as an envelope made of a plastic such as polyethylene which serves to reduce the rate of diffusion of the volatile constituents into the surrounding atmosphere. An example of this would be to place the gel in a dish or cup and then cover the dish with a laminate seal which will inhibit diffusion until the seal is removed prior to use.

A very practical and preferred way of regulating the rate of release of odorant from the gel is by forming the gel in a dish thereby providing a single surface, and then placing the dish in a holder which is completely enclosed but having vents or ventlike openings whereby the holder may be in an open position or in a closed position or at any stage in between. When the gels are not in use, the holder can merely be turned to the "off" position until such time as further use is desired. When the gel is depleted, the dish can simply be removed from the holder and replaced with a similar dish containing fresh gel.

A further attractive feature of the present gels is that they shrink at a predictable rate which is directly proportional to the loss of volatile constituents. This property can be utilized to give a visual indication of when the gel requires replacement. This can be accomplished by providing indicia on the bottom of the dish containing the gel (e.g., the word "replace") which can be viewed through a transparent opening in the holder. As the gel shrinks in thickness through loss of the volatile constituents, the indicia will become visible giving a visual signal of when the gel is exhausted and requires replacement.

Reodorant gels in accordance with the invention ca be conveniently made by adding polyvinyl acetal resin in the form of a powder to the liquid gelling agent (plus diluent and fragrances if desired) with stirring to secure a homogeneous mixture which can be filled into suitable containers or into the holder itself. Upon setting the mixture will form into a firm, dry gel. If desired, the gellation state may be expedited by subjecting the mixture to an elevated temperature of about 50°C to 150°C before or after filling. The period of heating can vary from a few minutes to 5 hours or longer. After cooling to ambient temperature a firm, rubbery gel is formed which is dry to the touch. Alternatively the gel may be prepared directly in a mold, container or the holder in which it is to be used. The gels can further be formulated by casting, injection molding, extrusion of dry blends and other conventional means.

The gels can be formed in any desired shape such as sheets, rods, cubes, discs and strips, and can have one or more generating surfaces.

Upon storing, the shelf-like of these gels is satisfactory over an extended period of time with no evidence of odor shift or deterioration of fragrance. Preferably the gels are stored in an air-tight atmosphere, for example encased in a laminated plastic film or in a metallic pouch, or in a plastic or metallic dish covered with a laminate seal.

If desired, small amounts of non-volatile plasticizers conventionally used for plasticization of thermoplastic resins can be added without adversely affecting the properties of the gels. Moreover these plasticizers also tend to increase the porosity of gel in the final stage which will permit the composition to be more completely depleted of the fragrance contained therein. Examples of such plasticizers are the lower alkyl esters of dibasic carboxylic acids such as dibutylphthalate, dioctylphthalate, di-2-ethylhexylphthalate, dioctyladipate, diisobutyladipate and the like.

Other conventional additives such as antioxidants, surfactants, dyes, deodorants, stabilizers, etc., can also be incorporated into the gels of the present invention.

The invention will now be further described by means of the following examples which are representative only, and should not be construed as limiting.

EXAMPLE I

Ten grams of a polyvinyl butyral polymer having an average molecular weight of about 1.8 to 2.7 × 10⁵ and containing about 80% by weight of polyvinyl butyral units, 18–21% by weight of polyvinyl alcohol units and 0–2% by weight polyvinyl acetate units was placed in a 4 oz polyethylene bottle and a well-mixed solution of 20 grams of methyl salicylate, 15 grams of limonene and 3 grams of a commercial floral fragrance was added with stirring. The mixture was cured in an electric oven at 80°C for three hours. The cooled gel (47.5 g) was firm, rubbery and dry to the touch.

EXAMPLE II

Three gels in accordance with the invention were prepared by combining the powdered PVB used in Example I with the ingredients in the amount indicated below with mixing to form a homogeneous solution. The gels were cured at about 100°C for a period of about two to four hours. The cooled gels were firm, rubbery solids which were dry to the touch.

| Ingredients | A | % w B | C |
|---|---|---|---|
| PVB | 20 | 20 | 20 |
| Methyl Salicylate | 80 | | 40 |
| Amyl Salicylate | | 40 | |
| Limonene | | 30 | 30 |
| Fragrance (floral-citrus | | 10 | 10 |

The salicylate gels such as oil of wintergreen (methyl salicylate) while being pleasant smelling are considerably enhanced by the addition of a diluent and additional fragrance. The above gels with the addition of the floral-citrus fragrance were rated efficacious as air fresheners over a six week period by a consumer testing panel. This compares to an efficacious period of only 12 to 15 days for a leading commercial aqueous-based reodorant gel, used under identical conditions of exposure.

EXAMPLE III

Seven gels in accordance with the invention were prepared by mixing the powdered PVB used in Example I with various gelling agents and optionally a diluent and a commercial fragrance in the proportions shown in Table B. After curing and weighing, the gels were placed into holders, some of which could be turned to an "on" or "off" position, and evaluated by a consumer test panel to determine their acceptability. At the end of their effective use life they were again weighed and weight loss recorded and average vaporization rate (mg/hr) calculated. The formulations tested were as follows.

| Ingredient | D | E | F | G | H | I | J |
|---|---|---|---|---|---|---|---|
| PVB | 20 | 15 | 20 | 20 | 24 | 24 | 21 |
| Methyl Salicylate | 40 | 38 | 40 | 30 | | | |
| Amyl Salicylate | | | | | 60 | 60 | 42 |
| Limonene | 40 | 38 | 30 | 40 | | | 31 |
| Fragrance | | 9ₐ | 10ᵦ | 10꜀ | 16ᵦ | 16_d | 6ₑ |

ₐCommercial Orange Fragrance
ᵦCommercial Floral-Citrus Fragrance
꜀Commercial Honeysuckle Fragrance
_dCommercial Citrus Fragrance
ₑCommercial Cherry Fragrance The results of testing were as follows.

| Formulation | Initial Weight (g) | On-Off Holder Used | Use Life[c] (Days) | Cumulative Wt. Loss (g) | Average Vap. Rate (mg/hr) | Comment |
|---|---|---|---|---|---|---|
| D | 75 | Yes | 63 | 35 | 23 | a) |
| E | 100 | Yes | 69 | 61 | 37 | |
| F | 60 | No | 46 | 29 | 26 | |
| G | 75 | No | 22 | 31 | 59 | b) |
| H | 50 | Yes | 39 | 2 | 3 | |
| I | 50 | Yes | 36 | 8 | 9 | |
| J | 50 | No | 28 | 9 | 13 | a) | a)Neutralized unpleasant odors.
b)Masked odor in entomology insectory — still effective when withdrawn from test.
c)Panel response varies due to olefactory sensitivity of individuals and concentration of fragrance in the available air space.

EXAMPLE IV

One gram of PVB as described in Example I, was placed in a 50 ml beaker and sufficient of the following liquids were mixed to "wet" all of the PVB and leave an excess of liquid. Following initial gellation the gels were cured at 100°C for 45 minutes. The length of time required for gellation and the appearance of the gels after curing are recorded in the following table.

| Formulation | Gellant | Gellation Time | Appearance After Curing |
|---|---|---|---|
| K | methyl salicylate | ½ – 1 min. | dry, firm and rubbery |
| L | ethyl salicylate | ½ – 1 min. | dry, firm and rubbery |
| M | eugenol | only slight setting-up | quite sticky, not firm or rubbery |

It is noteworthy that the salicylate formulations (K and L) both resulted in dry rubbery gels while formulation M containing a related methoxy substituted phenol did not. Moreover, it has been found that the polyvinyl acetal resins in accordance with the invention will not form gels with limonene although this compound is a satisfactory diluent for use in the present compositions.

EXAMPLE V

The following compositions are further illustrative of the gel compositions in accordance with the invention. The concentrations of ingredients are expressed in percent by weight of the total composition.

| Formulation | Gellant Type | Amount | Resin Type | Amount | Diluent Type | amount | Fragrance Type | Amount |
|---|---|---|---|---|---|---|---|---|
| N | amyl salicylate | 40 | a | 20 | amyl acetate | 34 | citrus | 6 |
| O | ethyl salicylate | 35 | b | 25 | pinene | 40 | — | — |
| P | methyl salicylate | 30 | c | 18 | limonene | 32 | — | — |
|   |   |   |   |   | water | 4 |   |   |
|   |   |   |   |   | Triton X-100 | 6 |   |   | a — polyvinyl butyral having an average molecular weight (weight average) of 1.0 to 1.5 × 10⁵ and containing approximately 80% by weight polyvinyl butyral units, 17.5–21.0% by weight polyvinyl alcohol units and 0–2.5% by weight of polyvinyl acetate units.

b — polyvinyl butyral having an average molecular weight of 0.38 to 0.45 × 10⁵ and containing approximately 80% by weight polyvinyl butyral units, 18.0–20.0% by weight polyvinyl alcohol units and 0–1.0% by weight polyvinyl acetate units.

c — polyvinyl butyral as used in Example I.

What is claimed is:

1. A gelled slow-release air reodorant composition comprising (1) as a fragrance from about 5 to about 90% by weight of a $C_1$ to $C_8$ alkyl salicylate in gelling interaction with (2) from about 10 to about 40% by weight of a polyvinyl acetal resin compatible with said salicylate, said polyvinyl acetal resin having a molecular weight of from about 30,000 to about 1,000,000 and consisting essentially of repeating vinyl acetal, vinyl alcohol and vinyl acetate groups represented by the structure:

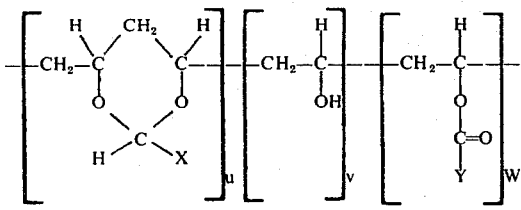

wherein X is H, alkyl of 1–8 carbon atoms, haloalkyl of 1–8 carbon atoms, hydroxyalkyl of 1  8 carbon atoms, alkenyl of 2–8 carbon atoms, halogen or hydroxyl; Y is alkyl of 1–9 carbon atoms; and $u$, $v$ and $w$ indicate the relative percent by weight of the respective vinyl acetal, vinyl alcohol, and vinyl ester groupings of the resin, and wherein $u$ is from about 30 to about 90, $v$ is from about 15 to about 25 and $w$ is from 0 to about 30, and the sum of $u + v + w$ equals 100.

2. The composition of claim 1 wherein X is $C_3H_7$ and Y is $CH_3$.

3. The composition of claim 2 wherein the reodorant gel additionally contains from 0 to about 85% by weight of perfume, 0 to about 20% water and 0 to about 60% by weight organic diluent, said organic diluent being mutually compatible with said alkyl salicylate gellant and said perfume.

4. The composition of claim 3 wherein $u$ is from about 75 to about 85, $v$ is from about 17 to about 21, and $w$ is from 0 to about 5, and the average molecular weight of the polyvinyl acetal resin is from about 180,000 to about 300,000.

5. The composition of claim 4 wherein the amount of alkyl salicylate is from about 10 to about 30% by weight, the amount of the resin is from about 15 to about 30% by weight, the amount of organic diluent is from about 10 to about 50% by weight, the amount of perfume is from about 1 to about 60% by weight and the amount of water is from 0 to about 10% by weight.

6. The composition of claim 5 wherein the diluent is a menthadiene.

7. The composition of claim 6 wherein the alkyl salicylate is methyl salicylate, ethyl salicylate or amyl salicylate.

8. The composition of claim 7 wherein the diluent is d- or l-limonene.

9. The composition of claim 6 wherein the alkyl salicylate is methyl salicylate.

* * * * *